(12) United States Patent
Massetti et al.

(10) Patent No.: US 9,520,439 B2
(45) Date of Patent: Dec. 13, 2016

(54) X-RAY AND OPTICAL IMAGE SENSOR

(71) Applicant: OMNIVISION TECHNOLOGIES, INC., Santa Clara, CA (US)

(72) Inventors: Dominic Massetti, San Jose, CA (US); Yu Zheng, San Jose, CA (US)

(73) Assignee: OmniVision Technologies, Inc., Santa Clara, CA (US)

( * ) Notice: Subject to any disclaimer, the term of this patent is extended or adjusted under 35 U.S.C. 154(b) by 93 days.

(21) Appl. No.: 14/034,210

(22) Filed: Sep. 23, 2013

(65) Prior Publication Data

US 2015/0085978 A1 Mar. 26, 2015

(51) Int. Cl.
*H01L 27/146* (2006.01)
*G01T 1/20* (2006.01)
*G01N 23/083* (2006.01)

(52) U.S. Cl.
CPC ....... *H01L 27/14676* (2013.01); *G01N 23/083* (2013.01); *G01T 1/2018* (2013.01); *H01L 27/1464* (2013.01); *H01L 27/14643* (2013.01); *H01L 27/14685* (2013.01)

(58) Field of Classification Search
USPC .................................................. 378/98, 98.8
See application file for complete search history.

(56) References Cited

U.S. PATENT DOCUMENTS

| | | | | |
|---|---|---|---|---|
| 5,617,463 A | * | 4/1997 | Beierlein | G01T 1/2018 348/E5.086 |
| 5,864,146 A | * | 1/1999 | Karellas | A61B 6/4258 250/581 |
| 5,909,029 A | | 6/1999 | Tonami et al. | |
| 6,895,077 B2 | * | 5/2005 | Karellas et al. | 378/98.3 |
| 7,180,075 B2 | * | 2/2007 | Brabec | G01T 1/2018 250/370.11 |
| 8,821,017 B2 | * | 9/2014 | Lalena et al. | 378/206 |
| 9,234,967 B2 | * | 1/2016 | Batkilin | G01T 1/20 |
| 2004/0099827 A1 | | 5/2004 | Yasuda | |

(Continued)

FOREIGN PATENT DOCUMENTS

| | | |
|---|---|---|
| CN | 101160102 A | 4/2008 |
| CN | 101561505 A | 10/2009 |

(Continued)

OTHER PUBLICATIONS

Bai, Y. et al., "Teledyne Imaging Sensors: Silicon CMOS imaging technologies for x-ray, UV, visible and near infrared," Proceedings of the SPIE Conference on Astronomical Instrumentation (2008, Marseille, France), Copyright 2008 Society of Photo-Optical Instrumentation Engineers, pp. 1-16.

(Continued)

*Primary Examiner* — Phillip A Johnston
(74) *Attorney, Agent, or Firm* — Blakely Sokoloff Taylor & Zafman LLP (57) ABSTRACT

An image sensor for capturing X-ray image data and optical image data includes an X-ray absorption layer and a plurality of photodiodes disposed in a semiconductor layer. The X-ray absorption layer is configured to emit photons in response to receiving X-ray radiation. The plurality of photodiodes disposed in the semiconductor layer is optically coupled to receive image light to generate the optical image data, and is optically coupled to receive photons from the X-ray absorption layer to generate X-ray image data.

17 Claims, 8 Drawing Sheets

(56) References Cited

U.S. PATENT DOCUMENTS

| | | | |
|---|---|---|---|
| 2006/0201546 A1* | 9/2006 | Yokoyama | 136/263 |
| 2008/0245968 A1* | 10/2008 | Tredwell et al. | 250/370.09 |
| 2009/0034687 A1 | 2/2009 | Ayraud | |
| 2012/0181439 A1 | 7/2012 | Cao et al. | |
| 2013/0114789 A1* | 5/2013 | Barbato | G01T 1/2018 378/62 |

FOREIGN PATENT DOCUMENTS

| | | |
|---|---|---|
| CN | 201469288 U | 5/2010 |
| TW | 2009-42854 A | 10/2009 |
| TW | 2012-22796 A | 6/2012 |

OTHER PUBLICATIONS

Morse, J., "Detectors for Imaging and Microanalysis," Slideshow Presentation, School on X-ray Imaging Techniques at the ESRF, Grenoble, France, Feb. 5-6, 2007, Retrieved from: http://www.esrf.eu/files/live/sites/www/files/events/conferences/xray-imaging-school/Presentations/02_Morse.pdf (29 pages).

TW 103108001—Office Action with English Translation, issued Sep. 16, 2015, 5 pages.

CN Application No. 201410063553.1—Chinese Office Action and Search Report, with English Translation, issued May 4, 2016 (32 pages).

\* cited by examiner

X-RAY AND OPTICAL IMAGE SENSOR

TECHNICAL FIELD

This disclosure relates generally to image sensors, and in particular but not exclusively, relates to combination X-ray and visible light image sensors.

BACKGROUND INFORMATION

X-ray detectors and imagers are used in a variety of medical and industrial processes. In many of these applications, it is undesirable for the imaged object to be subjected to prolonged X-ray exposure, as X-rays are known to damage both organic and inorganic materials. For instance, in medical applications, prolonged exposure to X-rays has been linked to serious health conditions. In conventional X-ray technologies, multiple X-rays may need to be taken in order to obtain a quality X-ray image of the desired feature. Often times, this is the result of the X-ray equipment operator having to "guess and check" the location of the X-ray sensor in relation to the feature/object being imaged. The X-ray image sensor placement is based on a best "guess" and then an X-ray image is taken to "check" the location and hopefully render a clear image of the desired feature. This not only exposes the subject of these procedures to additional harmful X-ray radiation but also wastes time and resources. Accordingly, an X-ray sensor capable of providing positioning feedback prior to capturing an X-ray may limit unnecessary X-ray exposure and increase efficiency.

BRIEF DESCRIPTION OF THE DRAWINGS

Non-limiting and non-exhaustive embodiments of the invention are described with reference to the following figures, wherein like reference numerals refer to like parts throughout the various views unless otherwise specified.

DETAILED DESCRIPTION

Embodiments of an image sensor for capturing both optical image data and X-ray image data are described herein. In the following description, numerous specific details are set forth to provide a thorough understanding of the embodiments. One skilled in the relevant art will recognize, however, that the techniques described herein can be practiced without one or more of the specific details, or with other methods, components, materials, etc. In other instances, well-known structures, materials, or operations are not shown or described in detail to avoid obscuring certain aspects.

Reference throughout this specification to "one embodiment" or "an embodiment" or "one example" means that a particular feature, structure, or characteristic described in connection with the embodiment is included in at least one embodiment of the present invention. Thus, the appearances of the phrases "in one embodiment" or "in an embodiment" or "one example" in various places throughout this specification are not necessarily all referring to the same embodiment. Furthermore, the particular features, structures, or characteristics may be combined in any suitable manner in one or more embodiments.

Figure 1:
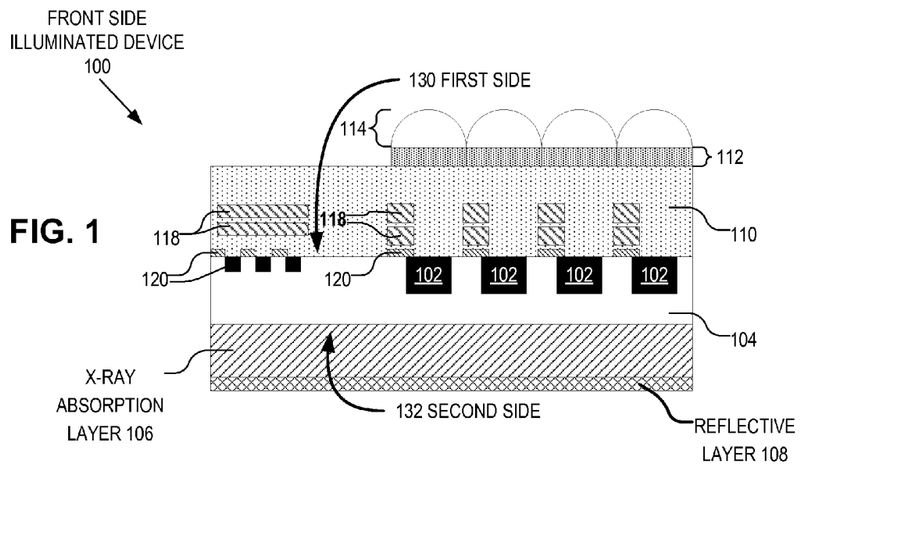
FIG. 1 is a cross section illustration of one possible example of a front side illuminated X-ray and optical image sensor ("XOIS") device architecture, in accordance with an embodiment of the disclosure.
Figure 2:
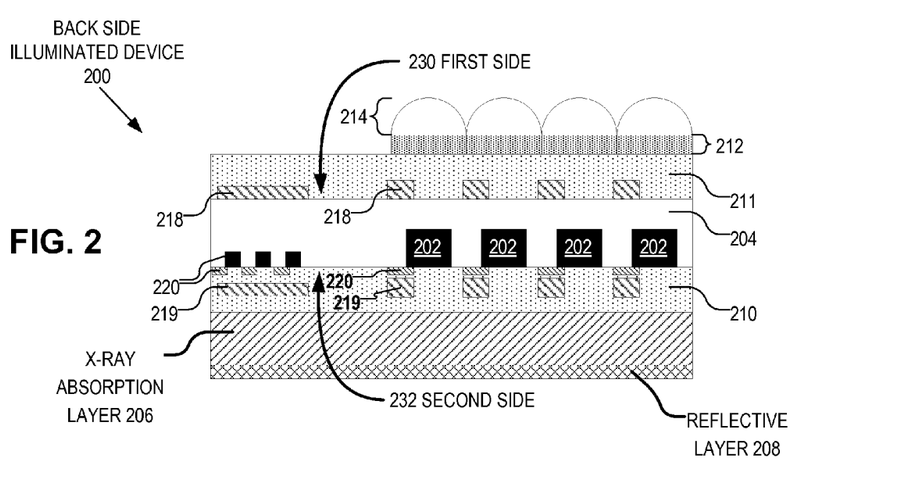
FIG. 2 is a cross section illustration one possible example of a back side illuminated XOIS device architecture, in accordance with an embodiment of the disclosure.

FIGS. 1 and 2 are cross section views showing two embodiments of possible device architectures for an X-ray and optical image sensor ("XOIS"), in accordance with an embodiment of the disclosure. FIG. 1 is a cross section illustration of one possible example of a front side illuminated XOIS 100 device architecture, in accordance with an embodiment of the disclosure. XOIS 100 includes a plurality of photodiodes 102 disposed in a semiconductor layer 104, in a front side illuminated configuration. In FIG. 1, semiconductor layer 104 has a first side 130 and a second side 132 opposite the first side 130. Since XOIS 100 is a front-side illuminated image sensor, first side 130 corresponds to the front side of semiconductor layer 104 and second side 132 corresponds to the back side of semiconductor layer 104. In one embodiment, the semiconductor layer 104 comprises silicon. An X-ray absorption layer 106 is disposed between the semiconductor layer 104 and a reflective layer 108. In one embodiment, reflective layer 108 is a metal such as aluminum and is 2 KÅ thick.

In FIG. 1, semiconductor layer 104 is disposed between the X-ray absorption layer 106 and the one or more intermediate layers 110. In the illustrated embodiment, intermediate layer(s) 110 includes X-ray shield layers 118 which are positioned to block X-ray radiation from reaching transistor components 120, which may be vulnerable to physical degradation from exposure to X-ray radiation. In some embodiments, X-ray shield layers 118 may also be electronic interconnects that are strategically positioned to also function as X-ray shields. X-ray shield layers 118 may include lead, tungsten, aluminum, and/or copper. Transistor components 120 are coupled to readout the plurality of photodiodes 102. For example, transistors components 120 may include transfer gates of transfer transistors (that are part of a "3T" or "4T" pixel architecture that is known in the art) for transferring photo-generated charge from photodiodes 102. Transistor components 120 may also include transistors that are part of peripheral readout circuitry for reading out each pixel in a pixel array that include the plurality of photodiodes 102.

In the illustrated embodiment, a color filter layer 112 is disposed between an array of microlenses 114 and intermediate layers 110. Microlenses 114 are configured to focus image light onto photodiodes 102. The color filter layer 112 may include red, green, and blue color filters, which may be arranged in a Bayer pattern.

FIG. 2 is a cross section illustration of one possible example of a backside illuminated XOIS 200 device architecture, in accordance with an embodiment of the disclosure. XOIS 200 includes a plurality of photodiodes 202 disposed in a semiconductor layer 204, in a back side illuminated configuration. In FIG. 2, semiconductor layer 204 has a first side 230 and a second side 232 opposite the first side 230. Since XOIS 200 is a back-side illuminated image sensor, first side 230 corresponds to the back side of semiconductor layer 204 and second side 232 corresponds to the front side of semiconductor layer 204. In one embodiment, the semiconductor layer 204 comprises silicon. An X-ray absorption layer 206 is disposed between the semiconductor layer 204 and a reflective layer 208. In one embodiment, reflective layer 208 is a metal such as aluminum and is 2 KÅ thick.

Intermediate layer(s) 210 is disposed between X-ray absorption layer 206 and semiconductor layer 204, as XOIS 200 is a backside illuminated architecture. Intermediate layer(s) 210 include metal interconnects 219 in the illustrated embodiment. In FIG. 2, intermediate layer 211 includes X-ray shield layers 218, which are positioned to block X-ray radiation from reaching transistor components 220, which may be vulnerable to physical degradation from exposure to X-ray radiation. X-ray shield layers 218 may include lead, tungsten, aluminum, and/or copper. Transistor components 220 are coupled to readout the plurality of photodiodes 202. For example, transistors components 220 may include transfer gates of transfer transistors (that are part of a "3T" or "4T" pixel architecture that is known in the art) for transferring photo-generated charge from photodiodes 202. Transistor components 220 may also include transistors that are part of peripheral readout circuitry for reading out each pixel in a pixel array that include the plurality of photodiodes 202.

Similar to FIG. 1, a color filter layer 212 is disposed between an array of microlenses 214 and intermediate layers 211, in FIG. 2. Microlenses 214 are configured to focus image light onto photodiodes 202. The color filter layer 212 may include red, green, and blue color filters, which may be arranged in a Bayer pattern.

Figure 3:
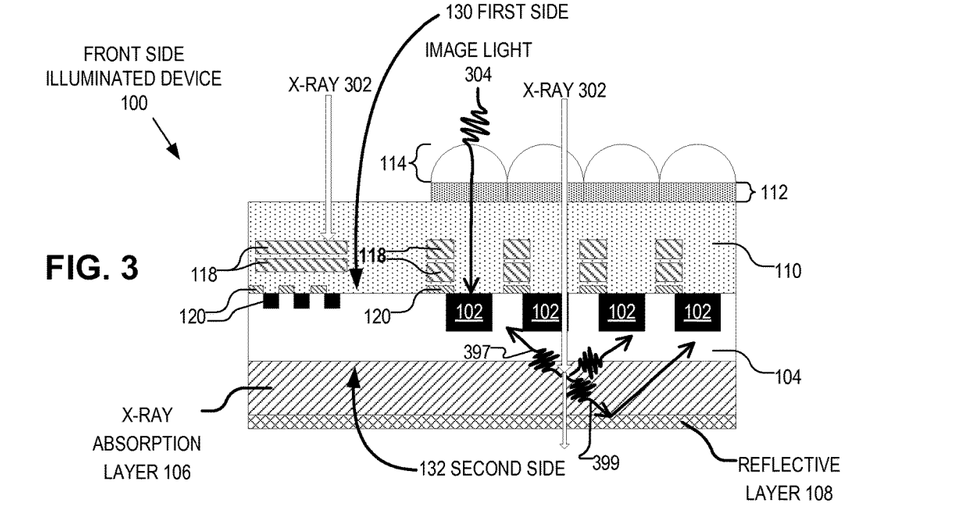
FIG. 3 is the XOIS device architecture of FIG. 1 in operation capturing both optical image data and X-ray image data, in accordance with an embodiment of the disclosure.

FIG. 3 is the XOIS 100 device architecture of FIG. 1 in operation capturing both optical image data and X-ray image data, in accordance with an embodiment of the disclosure. XOIS 100 is a dual mode imager capable of capturing both optical image data (e.g. visible and/or non-visible light) and X-ray image data from X-ray radiation. In FIG. 3, first side 130 is coupled to receive image light 304 and X-ray radiation 302.

In FIG. 3, image light 304 propagates through microlenses 114, color filter layer 112, intermediate layer 110, and into one of the photodiodes 102, in that order. In FIG. 3, image light 304 propagating in photodiode 102 generates image charge that can be read out as optical image data to generate an image. Image light 304 may be visible light or non-visible light (e.g. infrared or ultraviolet). Filters (not illustrated) may be included in a filter stack of XOIS 100 to keep certain wavelengths of light (e.g. infrared) from reaching photodiodes 102.

XOIS 100 is also capable of capturing X-ray image data. In FIG. 3, X-ray beam 302 propagates through microlenses 114, color filter layer 112, intermediate layer 110, and semiconductor layer 104, in that order. X-ray beam 302 may propagate through a photodiode 102 as it travels through semiconductor layer 104. In other words, X-ray absorption layer 106 is positioned to receive X-ray beam 302 through photodiodes in the plurality of photodiodes 102.

Generally, X-rays having energy greater than approximately 10 keV can pass through silicon with very low quantum efficiency (meaning the silicon does not convert the incident X-ray radiation into electrons). X-rays having energy greater than approximately 10 keV are sometimes used in medical diagnostics. X-rays having an energy less than 10 keV may be absorbed by silicon, similarly to visible light. Therefore, X-ray beam 302 having energy greater than approximately 10 keV may pass through semiconductor layer 104 if semiconductor layer 104 is silicon. Of course, semiconductor materials other than silicon may be used.

After propagating through semiconductor layer 104, X-ray beam 302 encounters X-ray absorption layer 106. X-ray absorption layer 106 is configured to emit photons in response to receiving (and being stimulated by) X-ray radiation. X-ray absorption layer 106 may be a phosphor such as Gadox (a.k.a. P43) having a composition of $Gd_2O_2S$:Tb. Gadox may emit photons having a wavelength of approximately 545 nm when it is stimulated by X-ray radiation. It should be noted that there are many materials/structures that emit light upon absorption of X-ray radiation that could be used as X-ray absorption layer 106. In FIG. 3, X-ray beam 302 stimulates X-ray absorption layer 106 to emit photons 397. Photons 397 move through (and are absorbed by) photodiodes 102 in semiconductor layer 104, which generates image charge in the photodiodes. Therefore, the plurality of photodiodes 102 can generate X-ray image data by measuring photons emitted by X-ray absorption layer 106 when X-ray radiation stimulates X-ray absorption layer 106 to emit photons.

In FIG. 3, X-ray absorption layer 106 is positioned between semiconductor layer 104 and a reflective layer 108. Reflective layer 108 is positioned to direct photons emitted by the X-ray absorption layer 106 back towards the plurality of photodiodes 102. In FIG. 3, X-ray beam 302 stimulates X-ray absorption layer 106 to emit photons 399. Photons 399 are emitted toward reflective layer 108, which reflects the photons 399 back to photodiodes 102 so that the photodiodes 102 can generate image charge from photons 399. In some embodiments, reflective layer 108 is not included in XOIS 100, but including reflective layer 108 may more efficiently measure the photons generated by X-ray beam 302 stimulating X-ray absorption layer 106. If reflective layer 108 is included in XOIS 100, X-ray beam 302 may propagate through the reflective layer 108 and any transparent handle substrate (not illustrated) that reflective layer 108 is disposed on.

FIG. 3 also shows that in the X-ray mode of operation, X-ray shield layers 118 disposed above transistor components 120 are positioned to block the X-rays 302 in order to limit damage to transistor components 120.

Figure 4:
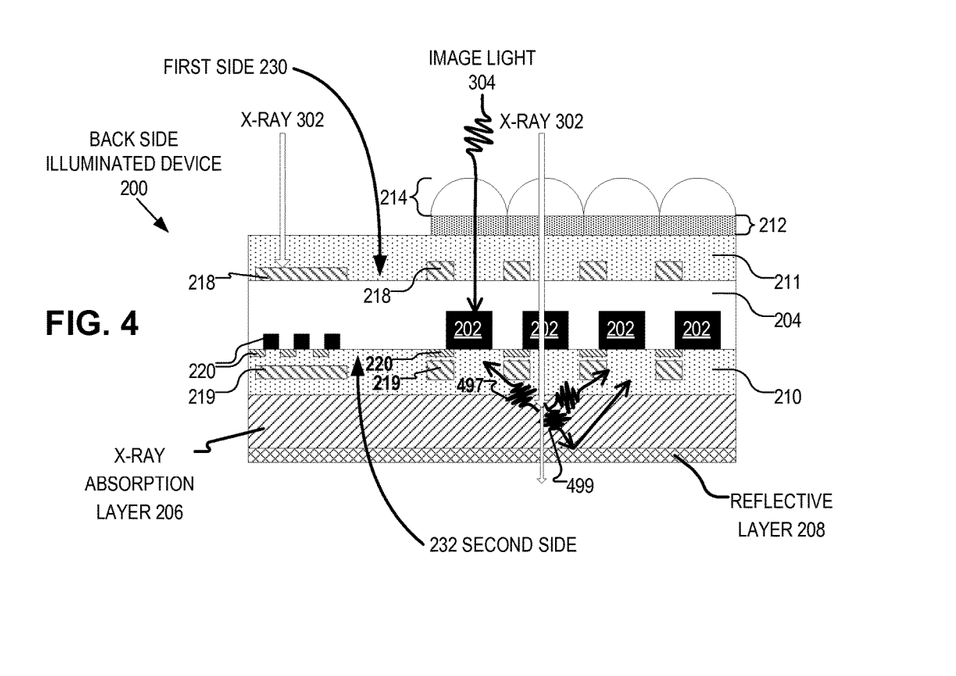
FIG. 4 is the XOIS device architecture of FIG. 2 in operation capturing both optical image data and X-ray image data, in accordance with an embodiment of the disclosure.

FIG. 4 illustrates the XOIS device architecture of FIG. 2 in operation capturing both optical image data and X-ray image data, in accordance with an embodiment of the disclosure. Similar to XOIS 100, XOIS 200 is a dual mode imager capable of capturing both optical image data (e.g. visible and/or non-visible light) and X-ray image data from X-ray radiation. In FIG. 4, first side 230 is coupled to receive image light 304 and X-ray beam 302.

In FIG. 4, image light 304 propagates through microlenses 214, color filter layer 212, intermediate layer 211, and into one of the photodiodes 202, in that order. In FIG. 4, image light 304 propagating in photodiode 202 generates image charge that can be read out as optical image data to generate an image. Image light 304 may be visible light or non-visible light (e.g. infrared or ultraviolet). Filters (not illustrated) may be included in a filter stack of XOIS 200 to keep certain wavelengths of light (e.g. infrared) from reaching photodiodes 202.

XOIS 200 is also capable of capturing X-ray image data. In FIG. 4, X-ray beam 302 propagates through microlenses 214, color filter layer 212, intermediate layer 211, semiconductor layer 204, and intermediate layer 210, in that order. X-ray beam 302 may propagate through a photodiode 202 as it travels through semiconductor layer 204. In other words, X-ray absorption layer 206 is positioned to receive X-ray beam 302 through photodiodes in the plurality of photodiodes 202.

As discussed above, X-rays having energy greater than approximately 10 keV can generally pass through silicon with very low quantum efficiency (meaning the silicon does not convert the incident X-ray radiation into electrons), while X-rays having an energy less than 10 keV may be absorbed by silicon. Therefore X-ray beam 302 having energy greater than approximately 10 keV may pass through semiconductor layer 204 if semiconductor layer 204 is silicon.

After propagating through intermediate layer 210, X-ray beam 302 encounters X-ray absorption layer 206. X-ray absorption layer 206 may generally have the same properties as X-ray absorption layer 106 and is configured to emit photons in response to receiving (and being stimulated by) X-ray radiation. In FIG. 4, X-ray beam 302 stimulates X-ray absorption layer 206 to emit photons 497. Photons 497 travel through intermediate layer 210 and into photodiodes 202 in semiconductor layer 204. Photons 497 generate image charge in photodiodes 202, which can then be readout as X-ray image data. Therefore, the plurality of photodiodes 202 can generate X-ray image data by measuring photons emitted by X-ray absorption layer 206 when X-ray radiation stimulates X-ray absorption layer 206 to emit photons.

In FIG. 4, X-ray absorption layer 206 is positioned between intermediate layer(s) 210 and a reflective layer 208. Reflective layer 208 is positioned to direct photons emitted by the X-ray absorption layer 206 back towards the plurality of photodiodes 202. In FIG. 4, X-ray beam 302 stimulates X-ray absorption layer 206 to emit photons 499. Photons 499 are emitted toward reflective layer 208, which reflects the photons 499 back to photodiodes 202 so that the photodiodes 202 can generate image charge from photons 499. In some embodiments, reflective layer 208 is not included, but including reflective layer 208 may more efficiently measure the photons generated by X-ray beam 302 stimulating X-ray absorption layer 206. If reflective layer 208 is included in XOIS 200, X-ray beam 302 may propagate through the reflective layer 208 and any transparent handle substrate (not illustrated) that reflective layer 208 is disposed on.

FIG. 4 also shows that in the X-ray mode of operation, X-ray shield layers 218 disposed above transistor components 220 are positioned to block the X-rays 302 in order to limit damage to transistor components 220.

Figure 7:
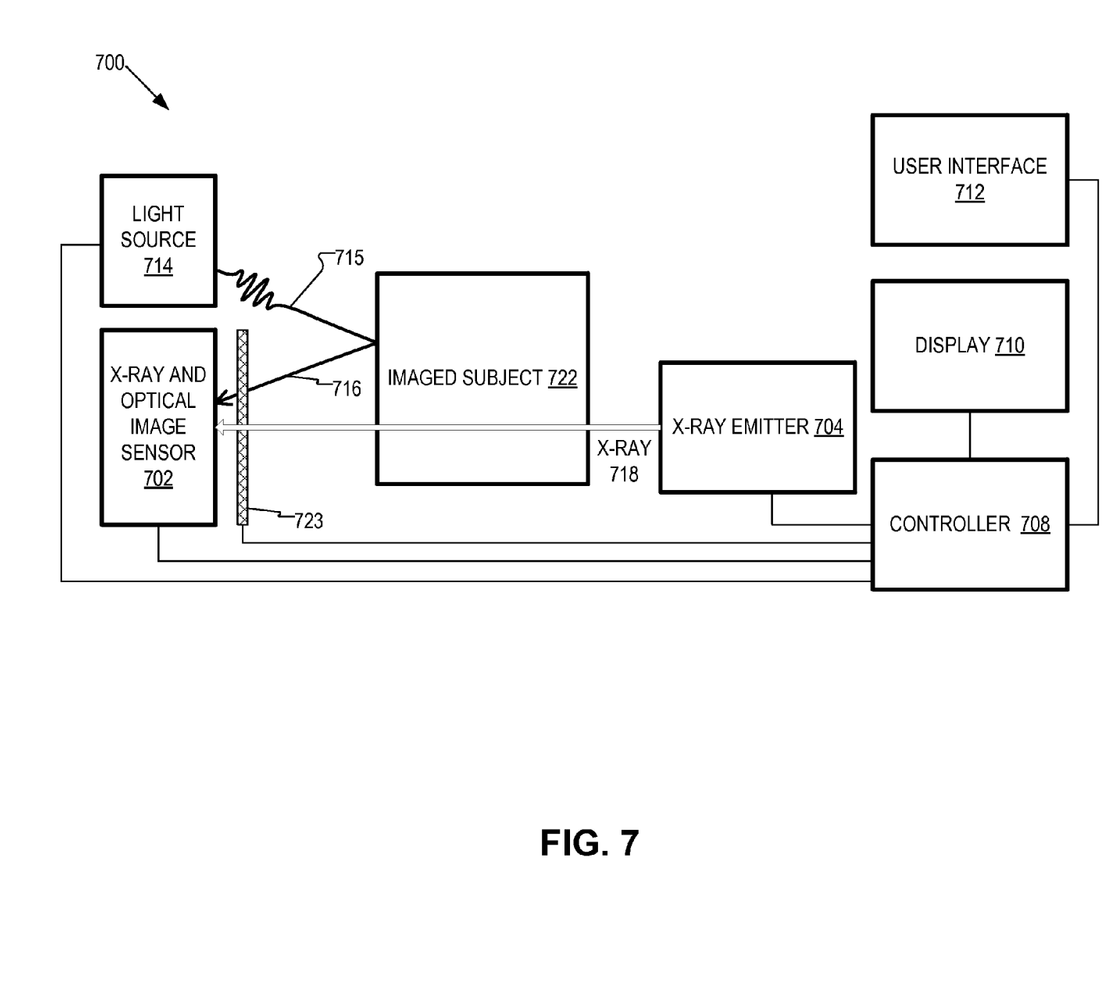
FIG. 7 is a diagram illustrating one example of an X-ray and optical imaging system, in accordance with an embodiment of the disclosure.

The discussion of FIGS. 1-4 shows that XOIS 100 and XOIS 200 are dual mode imagers capable of capturing X-ray image data and optical image data. FIG. 7 illustrates one example of an X-ray and optical imaging system 700 that can incorporate XOIS 100 or XOIS 200 as XOIS 702, in accordance with an embodiment of the disclosure.

In FIG. 7, controller 708 is coupled to control XOIS 702 to capture optical image data and X-ray image data and also coupled to receive the optical image data and X-ray image data from XOIS 702. XOIS 702 may have color filters arranged in patterns (e.g. a Bayer pattern) to capture color optical images or XOIS 702 may not have color filters and be configured to capture monochromatic optical images. Controller 708 may control operation parameters of XOIS 702 such as exposure duration (electronic shutter) and signal gain. Controller 708 may include a processor, a Field Programmable Gate Array ("FPGA"), or other logic for processing image data. Controller 708 may include memory for storing instructions, settings, and image data. In one embodiment, controller 708 is connected (wired or wirelessly) to the internet or local area network and may send X-ray image data or optical image data to another device via the internet or local area network.

Controller 708 is also coupled to X-ray emitter 704 to control the emission of X-ray beam 718 (which may have energy greater than 10 KeV) from X-ray emitter 704. X-ray emitter 704 may be included in a maneuverable hardware module so that the X-ray emitter 704 can be properly positioned to generate an image (in coordination with XOIS 702) of an imaged subject 722 (e.g. a tooth). Controller 708 may be coupled to control operation parameters of the X-ray emitter 704 such as energy of X-rays emitted, duration of X-ray beam 718, angle of X-rays emitted, and the location of X-ray emitter 704 relative to the XOIS 702. In one embodiment, controller 708 is wirelessly coupled to control, send, and receive data from X-ray emitter 704 and XOIS 702. In FIG. 7, controller 708 is coupled to control a light source 714 to emit source light 715. Light source 714 is optional, in some embodiments. Controller 708 is further coupled to a display 710, and user interface 712, in FIG. 7. The user interface may be a mouse, trackpad, selection switch and/or keyboard, or otherwise.

In FIG. 7, controller 708 is also coupled to control opening and closing of an optical shutter 723. Optical shutter 723 may be made from a material (e.g. a plastic) that blocks visible light from becoming incident onto XOIS 702, but still allows X-ray beam 718 to propagate through it. In one embodiment, optical shutter 723 includes a liquid crystal shutter layer and is integrated into XOIS 702 and disposed over photodiodes 102/202 to block out visible light. Optical shutter 723 may only be present in certain embodiments.

Figure 8:
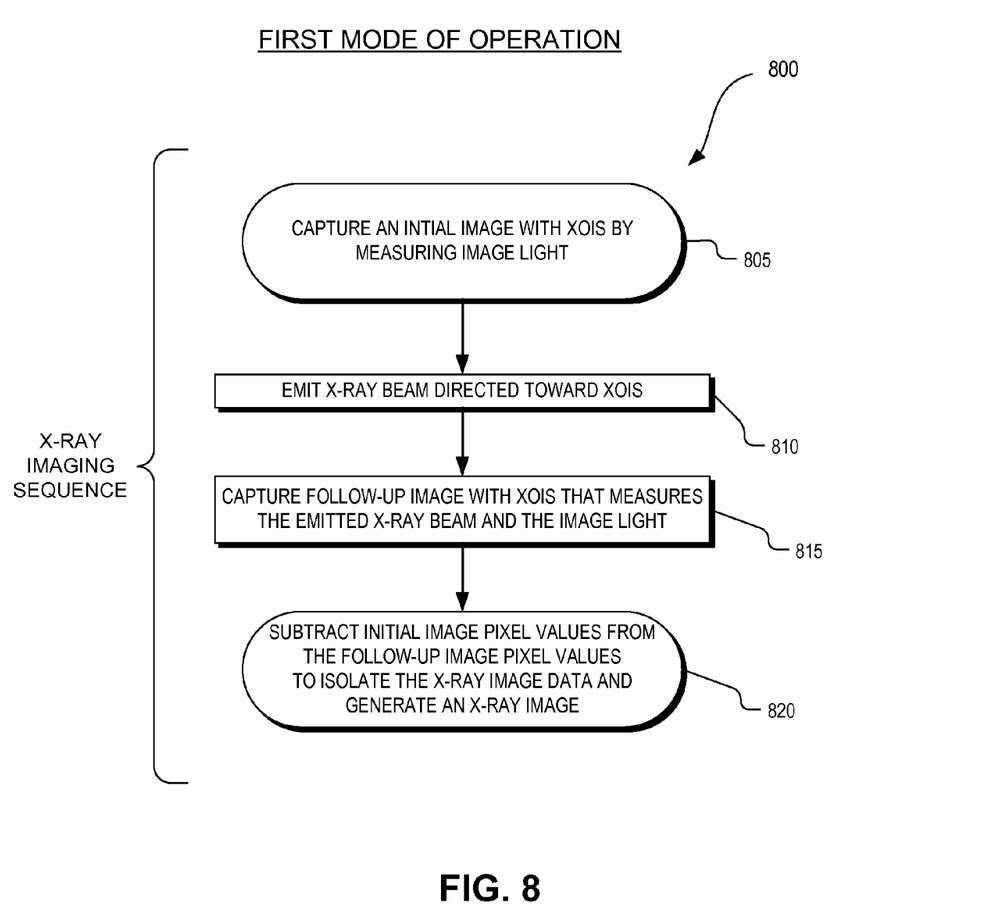
FIG. 8 is a flow chart illustrating a method of operating an X-ray and optical imaging system, in accordance with an embodiment of the disclosure.

X-ray and optical imaging system 700 may operate in a variety of different modes, depending on the use-case and the configuration of imaging system 700. FIG. 8 is a flow chart illustrating a method 800 of operating X-ray and optical imaging system 700, in accordance with an embodiment of the disclosure. The order in which some or all of the process blocks appear in process 800 should not be deemed limiting. Rather, one of ordinary skill in the art having the benefit of the present disclosure will understand that some of the process blocks may be executed in a variety of orders not illustrated, or even in parallel.

In a first mode of operation illustrated in FIG. 8, controller 708 directs XOIS 702 to captures an initial image by measuring image light 716 with its photodiodes (process block 805). An electronic shutter sequence (e.g. rolling or global shutter) may be used to measure the image charge on the photodiodes. After directing XOIS 702 to capture the initial image, controller 708 may cause X-ray emitter 704 to emit an X-ray beam 718 (process block 810) directed toward imaged subject 722 while controller 708 also causes XOIS 702 to capture a follow-up image (process block 815). The initial image includes optical image data from measuring image light 716 generating image charge on the photodiodes in XOIS 702, while the follow-up image includes both measurements of image light 716 and the portion of X-ray beam 718 that penetrates imaged subject 722, as the penetrating portion of X-ray beam 718 stimulates photons in the X-ray absorption layer (e.g. X-ray absorption layer 106 or 206) that are measureable by the photodiodes in XOIS 702. To isolate the X-ray image data, to generate an X-ray image, the initial image pixel values are subtracted from the follow-up image pixel values (process block 820) since the initial image includes optical image data (e.g. visible light) and the follow-up image includes both optical image data and X-ray image data. In other words, the initial image serves as a baseline/calibration image for the follow-up image. To improve results, the follow-up image may be captured directly after capturing the initial image. It is appreciated that the implementation of this first mode of operation does not necessarily require an optical shutter 723.

It is appreciated that an operator of imaging system 700 may view a series of images of imaged subject 722 captured by XOIS 702 in real-time in order to correctly position XOIS 702 to take an X-ray image of the imaged subject 722. The series of images (e.g. a video) may be displayed on display 710 by controller 708 to give the operator visual feedback as to the positioning of XOIS 702 with regard to imaged subject 722. Based on the visual feedback, the operator may interact with user interface 712 to initiate an X-ray imaging sequence. The X-ray imaging sequence may include capturing the initial image and then the follow-up image, as shown in FIG. 8. In one embodiment, ambient light provides enough light to capture the series of images. In other embodiments, light source 714 may be controlled by controller 708 to emit source light 715 at different intensities to provide enough light to reflect a measureable quantity of image light 716 for measurement by XOIS 702. In one embodiment, light source 714 is tuned to provide a relatively low level of source light 715 to ensure that the photodiodes in XOIS 702 are not at full capacity when they capture the initial image so there is still headroom to measure the additional image charge which will be generated by the portion of X-ray beam 718 that penetrates imaged subject 722 and stimulates X-ray absorption layer 106 or 206.

Figure 9:
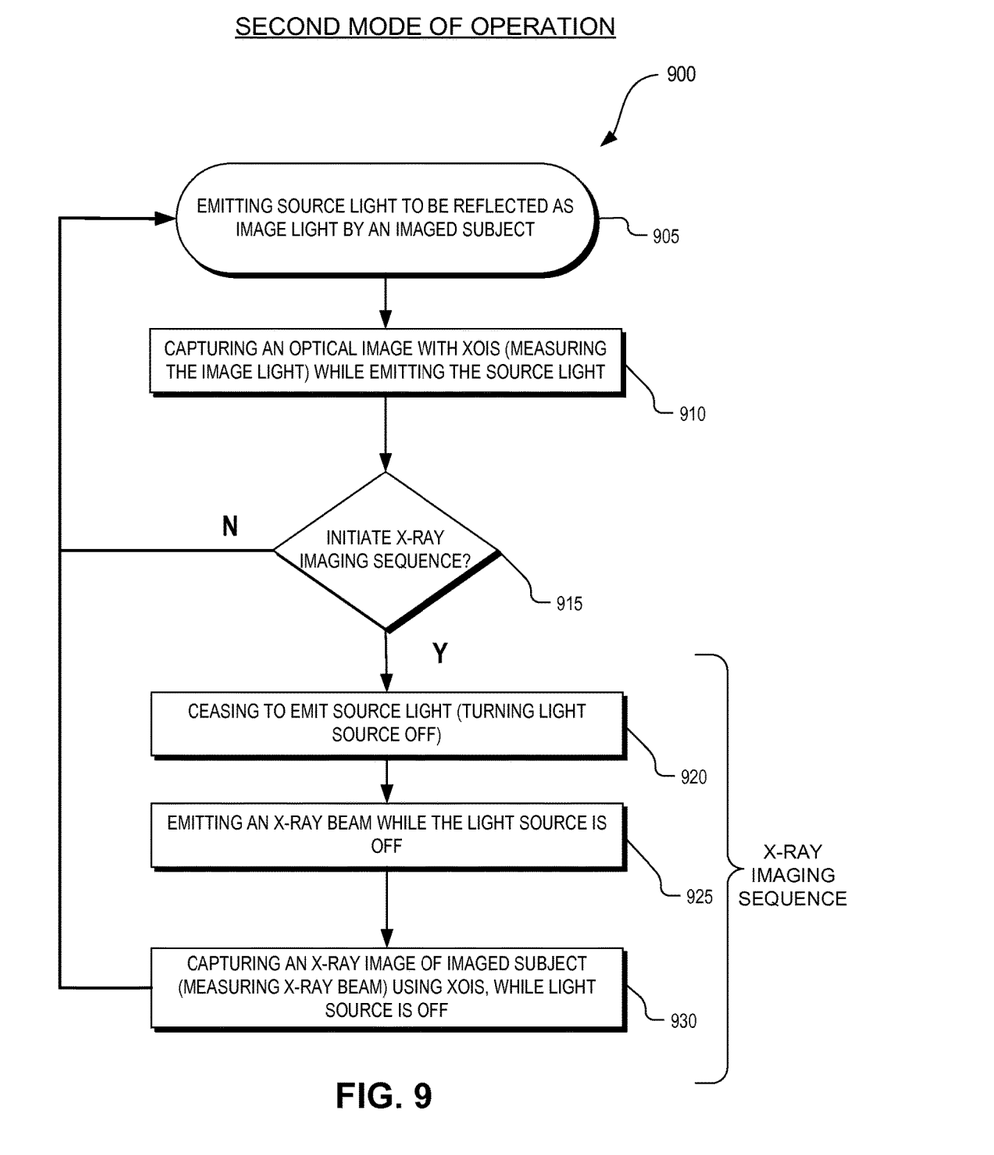
FIG. 9 is a flow chart illustrating a method of operating an X-ray and optical imaging system, in accordance with an embodiment of the disclosure.

FIG. 9 is a flow chart illustrating a method 900 of operating X-ray and optical imaging system 700, in accordance with an embodiment of the disclosure. The order in which some or all of the process blocks appear in process 900 should not be deemed limiting. Rather, one of ordinary skill in the art having the benefit of the present disclosure will understand that some of the process blocks may be executed in a variety of orders not illustrated, or even in parallel.

In a second mode of operation illustrated in FIG. 9, light source 714 is a non-visible light source (e.g. infrared or ultraviolet). Light source 714 may be configured to only emit a relatively narrow band of light. Light source 714 may include an infrared or ultraviolet light emitting diode ("LED"). A filter may be disposed in a filter stack over XOIS 702 so that XOIS 702 is configured to only measure the same band of source light 715 that is emitted by light source 714. In one embodiment, light source 714 emits infrared light centered around 850 nm and the filter over XOIS 702 only allows light between 800 and 900 nm to reach the photodiodes in XOIS 702. In this configuration, XOIS 702 does not measure visible light.

To generate an X-ray image in this second mode of operation, controller 708 causes light source 714 to emit source light 715 that is reflected by imaged subject 722 as image light 716 (process block 905). In process block 910, XOIS 702 captures an optical image (which may be monochromatic) by measuring image light 716. The optical image may be displayed on display 710 to give the operator visual feedback as to the positioning of XOIS 702 with regard to imaged subject 722. Based on the visual feedback, the operator may interact with user interface 712 to initiate an X-ray imaging sequence. At process block 915, controller 708 may receive a user interface signal from user interface 712 for initiating an X-ray imaging sequence. If controller 708 does not receive the user interface signal for initiating the X-ray imaging sequence, process 900 returns to process block 905. It is understood that process 900 may run in a loop comprising process block 905, 910, 915, and back to process block 905. This may capture a series of optical images that are displayed on display 710 as a video to assist an operator in positioning XOIS 702 to capture an X-ray image. When controller 708 initiates an X-ray imaging sequence, process 900 continues to process block 920 where light source 714 is turned off and controller 708 causes X-ray emitter 704 to emit an X-ray beam 718 (process block 925) directed toward imaged subject 722 while controller 708 also causes XOIS 702 to capture an X-ray image (process block 930). Since the filter on XOIS 702 prevents visible light from being measured by the photodiodes and light source 714 is turned off during the X-ray imaging sequence, the image charge measured by the photodiodes of XOIS 702 should be mostly (if not exclusively) generated by the portion of X-ray beam 718 that penetrates imaged subject 722, passes through the filters on XOIS 702, and stimulates photon emission on the X-ray absorption layer 106 or 206 that is measured by the photodiodes. Again, those skilled in the art will understand that optical shutter 723 is optional in this second mode of operation. After capturing the X-ray image in process block 930, process 900 returns to process block 905.

Figure 10:
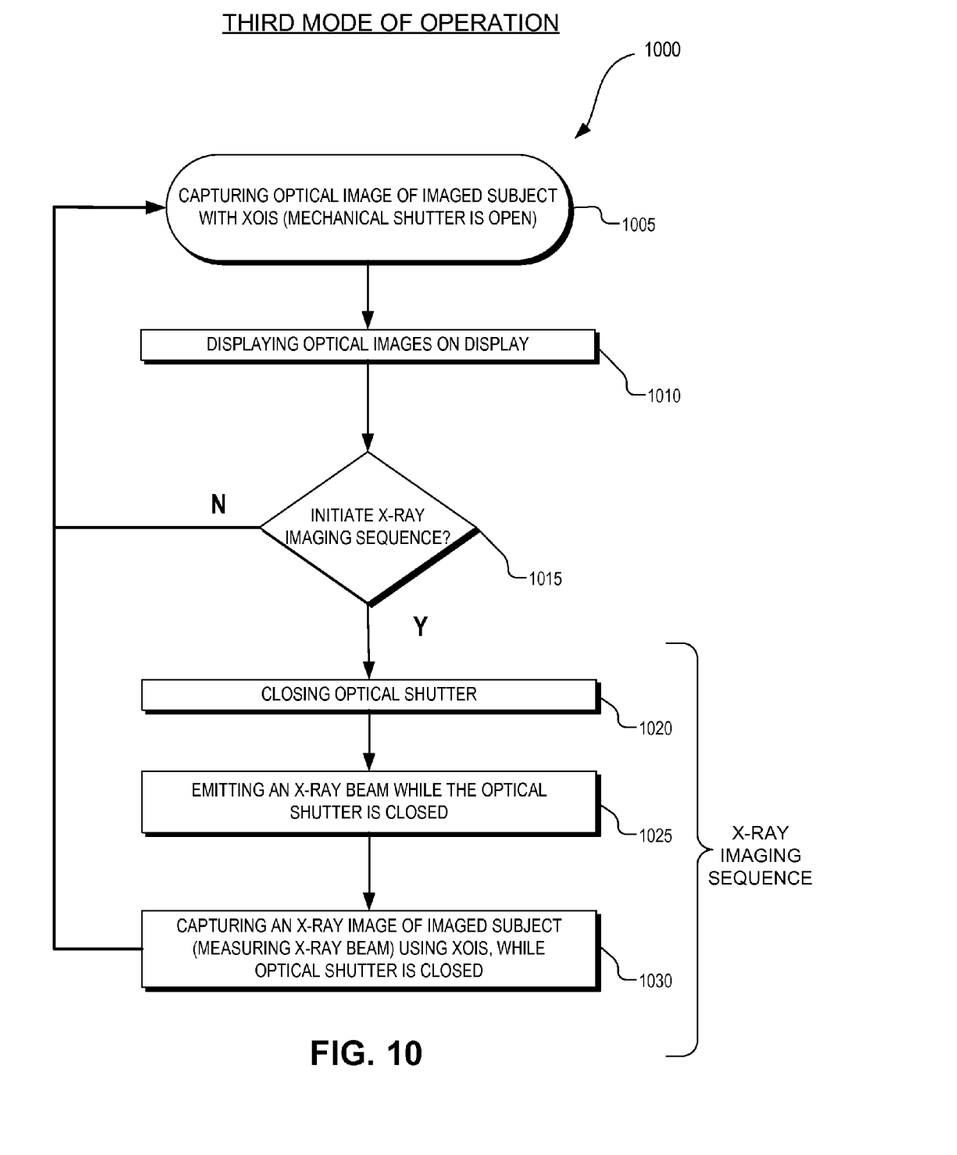
FIG. 10 is a flow chart illustrating a method of operating an X-ray and optical imaging system, in accordance with an embodiment of the disclosure.

FIG. 10 is a flow chart illustrating a method 1000 of operating X-ray and optical imaging system 700, in accordance with an embodiment of the disclosure. The order in which some or all of the process blocks appear in process 1000 should not be deemed limiting. Rather, one of ordinary skill in the art having the benefit of the present disclosure will understand that some of the process blocks may be executed in a variety of orders not illustrated, or even in parallel.

In a third mode of operation illustrated in FIG. 10, optical shutter 723 is utilized. While the operator is positioning XOIS 702 to image imaged subject 722, XOIS 702 is capturing images (process block 1005) and sending the images to controller 708 for display on display 710 as visual feedback (process block 1010). Once the operator of imaging system 700 determines that XOIS 702 is properly positioned to capture an X-ray image, she interacts with user interface 712 to initiate an X-ray imaging sequence. At process block 1015, controller 708 may receive a user interface signal from user interface 712 for initiating an X-ray imaging sequence. If controller 708 does not receive the user interface signal for initiating the X-ray imaging sequence, process 1000 returns to process block 1005. It is understood that process 1000 may run in a loop comprising process block 1005, 1010, 1015, and back to process block 1005. This may capture a series of optical images that are displayed on display 710 as a video to assist an operator in positioning XOIS 702 to capture an X-ray image. When controller 708 initiates an X-ray imaging sequence in response to receiving the user interface signal (or other signal), process 1000 continues to process block 1020. In process block 1020, optical shutter 723 is closed to block out image light 716 from propagating into the photodiodes of XOIS 702. After optical shutter 723 is closed, controller 708 causes X-ray emitter 704 to emit an X-ray beam 718 (process block 1025) directed toward imaged subject 722 while controller 708 also causes XOIS 702 to capture an X-ray image (process block 1030). The portion of X-ray beam 718 that penetrates imaged subject 722 also penetrates the optical shutter 723 and proceeds to stimulate photon emission on the X-ray absorption layer 106 or 206 that is measured by the photodiodes in XOIS 702. Since image light 716 is blocked by optical shutter 723 during an X-ray imaging sequence, XOIS 702 is only measuring the image charge generated by the X-ray beam 718 stimulating the X-ray absorption layer. In other words, closing the optical shutter 723 during the X-ray imaging sequence prevents external image light 716 from contributing image charge (and polluting) the image captured during the X-ray image sequence. After capturing the X-ray image in process block 1030, process 1000 returns to process block 1005.

In the first, second, and third mode of operating imaging system 700, the use of XOIS 702 allows an operator of the imaging system 700 to receive visual feedback as to the position of XOIS 702. Conventional X-ray sensors often lack a means for determining the X-ray sensor location/position with respect to the object being imaged. Frequently, operators of these devices employ a trial and error method of taking multiple X-ray images to obtain one quality picture. This results in the imaged subject (which may be a body part) receiving unnecessary exposure to X-ray radiation in addition to wasting time and imaging resources. However, by taking one or more optical images with XOIS 702 prior to capturing the X-ray image, the location of the X-ray imager (included in XOIS 702) can be optimized before X-ray radiation is used to capture the X-ray image.

It is appreciated that the first, second, and third mode of operating imaging system 700 are not exhaustive and that other methods can be used. In one context, imaging system 700 is used in a dentist office to X-ray a tooth or a group of teeth. In this context, XOIS 702 may provide visual feedback for the operator on display 710 while the patient's mouth is open providing ambient light for XOIS 702 to measure as image light. Once the operator determines that XOIS 702 is properly positioned near the correct tooth to be X-rayed, the operator may ask the patient to close her mouth while the X-ray image sequence (which includes emitting X-ray beam 718 while initiating an image capture on XOIS 702) is executed. In this context, the patient's mouth acts similarly to an optical shutter and blocks out ambient light from contributing image charge (and polluting) the X-ray image data.

In some embodiments, controller 708 may manipulate both X-ray image data and optical image data. For example controller 708 may increase/decrease contrast, highlight desired areas of the image, crop the images, adjust the aspect ratio, superimpose the X-ray and optical images, display X-ray and optical images side by side or picture-in picture, etc. It is appreciated that repeating the X-ray imaging sequence described in the first, second, and third mode of operating imaging system 700 would also allow for a series of X-ray images to be captured. Controller 708 may control whether X-ray emitter 704 and XOIS 702 will capture video and/or still X-ray/optical image data.

Figure 5:
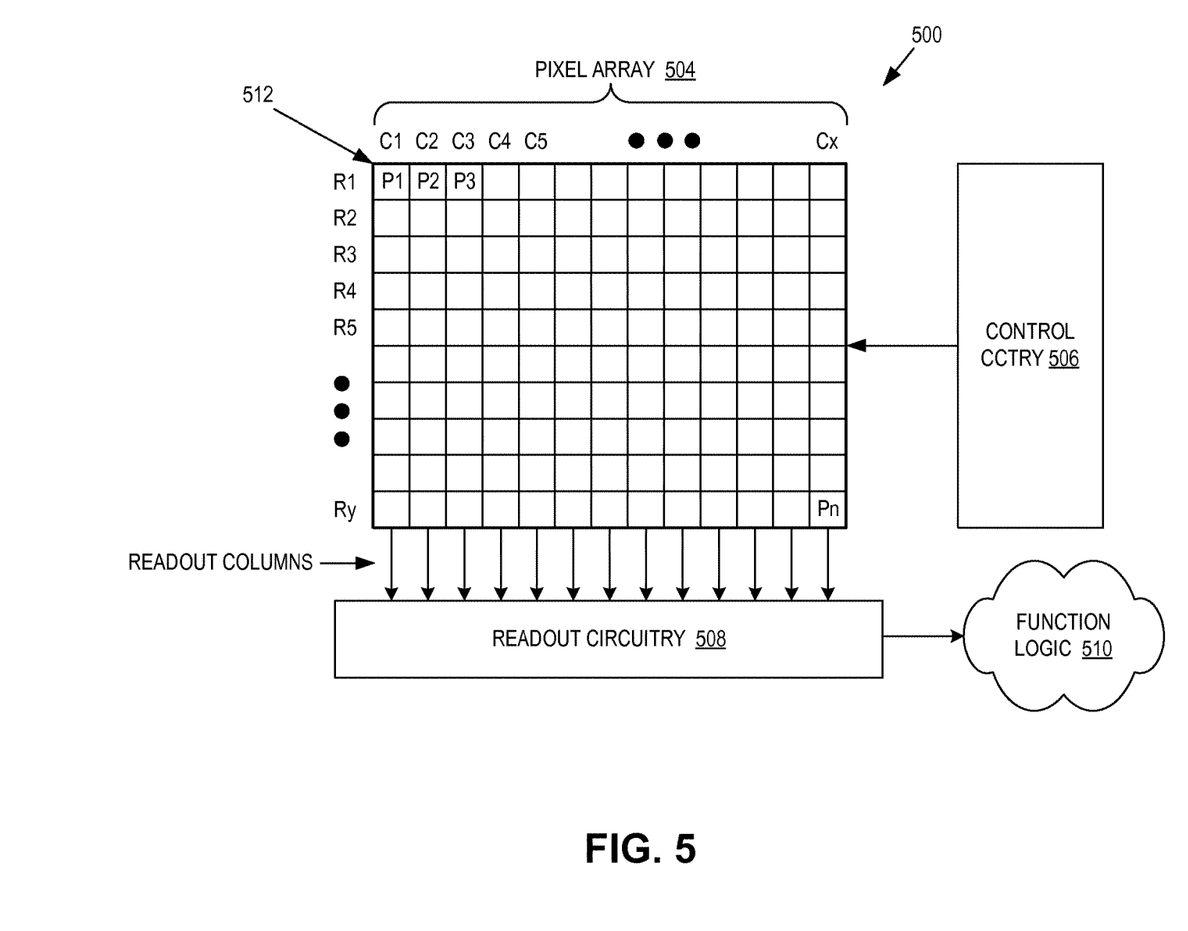
FIG. 5 illustrates a block diagram schematic of one example of an XOIS, in accordance with an embodiment of the disclosure.

FIG. 5 illustrates a block diagram schematic of one example of an XOIS 500, in accordance with an embodiment of the disclosure. FIG. 5 includes a pixel array 504 (including individual pixels 512 that would include photodiodes 102 or 202), control circuitry 506 coupled to the pixel array 504 to control operation of the pixel array 504, readout circuitry 508 coupled to the pixel array 504 to readout image data from the pixel array 504, and function logic 510 coupled to the readout circuitry 508 to store the image data readout from the pixel array 504.

In one embodiment, pixel array 504 is a two-dimensional array of photodiodes or pixels (e.g., pixels P1, P2, P3 ..., Pn). As illustrated, each pixel 512 can be arranged into a row (e.g., rows R1, R2, R3 ..., Ry) and column (e.g., column C1, C2, C3 ..., Cx) to acquire image data of an object, which can then be used to render an image of said object.

In one embodiment, after each pixel 512 receives image charge from image light 716 (whether originating from light source 714 or from an ambient light source) or image charge generated from X-ray absorption layer 106 or 206, the image data is read out by readout circuitry 508 and then transferred to function logic 510. In various embodiments, readout circuitry 508 may include amplification circuitry, analog-to-digital ("ADC") conversion circuitry, or otherwise. In one embodiment, readout circuitry 508 may read out one row of image data at a time along readout column lines (illustrated) or may read out the image data using a variety of other techniques (not illustrated), such as a serial read out or a full parallel read out of all pixels simultaneously. Function logic 510 may simply store the image data or even manipulate the image data by applying post image effects (e.g., crop, rotate, adjust brightness, adjust contrast, or otherwise). In one embodiment, the optical image data and/or the X-ray image data is a video feed. In this case, function logic 510 may manipulate the video feed.

In one embodiment, control circuitry 506 is coupled to pixel array 504 to control operational characteristics of pixel array 504. For example, control circuitry 506 may generate a shutter signal for controlling image acquisition. In one embodiment, the shutter signal is a global shutter signal for simultaneously enabling all pixels 512 within pixel array 504 to simultaneously capture their respective image data during a single acquisition window. In another embodiment, the shutter signal is a rolling shutter signal such that each row, column, or group of pixels 512 is sequentially enabled during consecutive acquisition windows.

Figure 6:
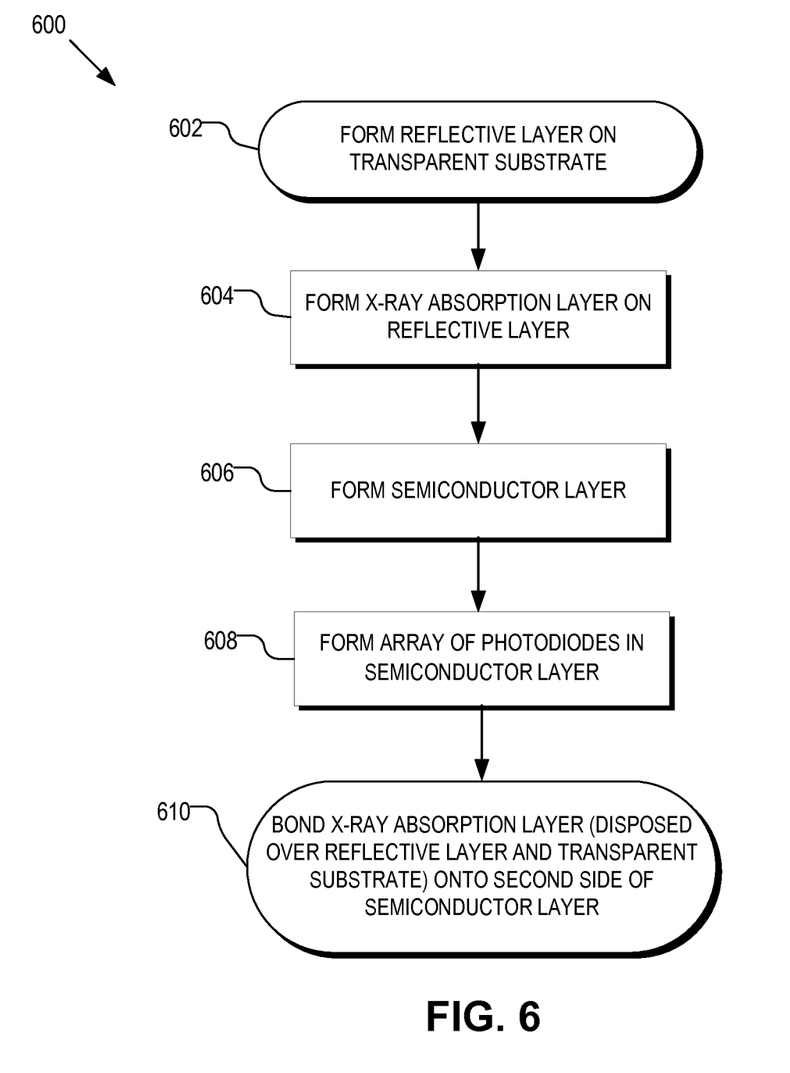
FIG. 6 is a flow chart illustrating one example of a method of forming an XIOS device, in accordance with an embodiment of the disclosure.

FIG. 6 is a flow chart illustrating one example of a process 600 of forming an XIOS device, in accordance with an embodiment of the disclosure. The order in which some or all of the process blocks appear in process 600 should not be deemed limiting. Rather, one of ordinary skill in the art having the benefit of the present disclosure will understand that some of the process blocks may be executed in a variety of orders not illustrated, or even in parallel.

In process block 602 a reflective layer (e.g. reflective layer 108 or 208) is formed on a transparent substrate (e.g. silicon or glass). In one embodiment, the reflective layer is a metal, such as aluminum. In process block 604, an X-ray absorption layer (e.g. X-ray absorption layer 106 or 206) is formed on the reflective layer. One skilled in the art will recognize that there are many possible materials/structures available that emit light with a wavelength capable of being detected by the plurality of photodiodes, when exposed to X-ray radiation. In one embodiment the X-ray absorption layer is a phosphor such as $Gd_2O_2S{:}Tb$ (P43).

A semiconductor layer is formed in process block 606. The semiconductor layer may be a silicon wafer that has been thinned to optimize device operation. In process block 608, an array of photodiodes (e.g. photodiodes 102 or 202) is formed in the semiconductor layer. Although the illustrated flowchart of process 600 shows forming the semiconductor layer subsequent to forming the X-ray absorption layer, the X-ray absorption layer may be formed subsequent to forming the semiconductor layer. In one example, the X-ray absorption layer is deposited onto the the semiconductor layer that already includes photodiodes. In another example, the X-ray absorption layer is deposited onto a metalized substrate (which may be the reflective layer) and then bonded to the semiconductor layer that already includes photodiodes.

In process block 610, the structure that includes the X-ray absorption layer and the reflective layer formed on the transparent substrate is bonded to the semiconductor layer such that a second side (e.g. second side 132 or 232) of the semiconductor layer is bonded to the X-ray absorption layer. It is appreciated that intermediate layers (including interconnects) may be formed between the layers recited in process 600, despite describing the layers as being "disposed on" or "formed on." In one example, an intermediate layer (e.g. intermediate layer 210) is disposed between the X-ray absorption layer and the semiconductor layer.

The above description of illustrated embodiments of the invention, including what is described in the Abstract, is not intended to be exhaustive or to limit the invention to the precise forms disclosed. While specific embodiments of, and examples for, the invention are described herein for illustrative purposes, various modifications are possible within the scope of the invention, as those skilled in the relevant art will recognize.

These modifications can be made to the invention in light of the above detailed description. The terms used in the following claims should not be construed to limit the invention to the specific embodiments disclosed in the specification. Rather, the scope of the invention is to be determined entirely by the following claims, which are to be construed in accordance with established doctrines of claim interpretation.

What is claimed is:

1. An image sensor for capturing X-ray image data of an object and optical image data of the object, the image sensor comprising:
    an X-ray absorption layer configured to emit photons in response to receiving X-ray radiation of the object;
    a plurality of photodiodes disposed in a semiconductor layer having a first side opposite a second side, wherein the plurality of photodiodes are optically coupled to receive image light of the object to generate the optical image data, and wherein the plurality of photodiodes are optically coupled to receive the photons from the X-ray absorption layer to generate the X-ray image data, the plurality of photodiodes positioned to receive the photons from the X-ray absorption layer through only the second side of the semiconductor layer and positioned to receive the image light through the first side of the semiconductor layer, wherein the image sensor is configured to receive the image light propagating from outside the image sensor, and wherein the X-ray absorption layer is disposed proximate to the second side of the semiconductor layer; and
    one or more microlenses disposed proximate to the first side of the semiconductor layer, wherein the X-ray radiation and the image light propagate through the one or more microlenses, and wherein the microlenses focus the image light into the plurality of photodiodes.

2. The image sensor of claim 1, further comprising a reflective layer positioned to direct the photons towards the plurality of photodiodes, wherein the X-ray absorption layer is disposed between the reflective layer and the second side of the semiconductor layer.

3. The image sensor of claim 2, wherein the reflective layer comprises aluminum.

4. The image sensor of claim 1, further comprising:
    one or more intermediate layers disposed between the second side of the semiconductor layer and the X-ray absorption layer; and
    electronic interconnects embedded in the one or more intermediate layers.

5. The image sensor of claim 1 further comprising:
    one or more intermediate layers disposed between the one or more microlenses and the first side of the semiconductor layer.

6. The image sensor of claim 1, wherein the X-ray absorption layer includes a phosphor.

7. The image sensor of claim 1, further comprising:
    transistors coupled to readout the plurality of photodiodes; and
    X-ray shield layers positioned to block the X-ray radiation from reaching the transistors.

8. The image sensor of claim 7, wherein the X-ray shield layers comprise metal.

9. The image sensor of claim 1, wherein the X-ray absorption layer is positioned to receive the X-ray radiation through the plurality of photodiodes.

10. The image sensor of claim 1, further comprising:
    readout circuitry coupled to the plurality of photodiodes to readout the optical image data and the X-ray image data from the plurality of photodiodes.

11. The image sensor of claim 1, wherein the plurality of photodiodes is arranged into a pixel array comprising rows and columns.

12. An imaging system comprising:
    an X-ray emitter for emitting an X-ray beam toward an object;
    a controller coupled to the X-ray emitter to control the emission of the X-ray beam; and
    an image sensor for capturing X-ray image data of the object and optical image data of the object, wherein the controller is coupled to the image sensor to control image capture, the image sensor comprising:
        an X-ray absorption layer configured to emit photons in response to receiving the X-ray beam;
        a plurality of photodiodes disposed in a semiconductor layer having a first side opposite a second side, wherein the plurality of photodiodes are optically coupled to receive image light of the object to generate the optical image data, and wherein the plurality of photodiodes are optically coupled to receive the photons from the X-ray absorption layer to generate the X-ray image data, the plurality of photodiodes positioned to receive the photons from the X-ray absorption layer through only the second side of the semiconductor layer and positioned to receive the image light through the first side of the semiconductor layer, wherein the image sensor is configured to receive the image light from outside the image sensor, and wherein the X-ray absorption layer is disposed proximate to the second side of the semiconductor layer; and
        one or more microlenses disposed proximate to the first side of the semiconductor layer, wherein the X-ray beam and the image light propagate through the one or more microlenses, and wherein the microlenses focus the image light into the plurality of photodiodes.

13. The imaging system of claim 12 further comprising a light source coupled to provide source light to a subject to be imaged, wherein the controller is coupled to the light source to control emissions of the source light.

14. The imaging system of claim 13, wherein the source light emitted by the light source is non-visible light, and wherein the image sensor includes a filter that filters out visible light from reaching the plurality of photodiodes.

15. A method of fabricating an image sensor for capturing X-ray image data of an object and optical image data of the object, the method comprising:
   forming an X-ray absorption layer configured to emit photons in response to receiving X-ray radiation of an object;
   forming a plurality of photodiodes in a semiconductor layer having a first side opposite a second side, wherein the plurality of photodiodes are optically coupled to receive image light to generate the optical image data, and wherein the plurality of photodiodes are optically coupled to receive the photons from the X-ray absorption layer to generate the X-ray image data, the plurality of photodiodes positioned to receive the photons from the X-ray absorption layer through only the second side of the semiconductor layer and positioned to receive the image light through the first side of the semiconductor layer, wherein the image sensor is configured to receive the image light propagating from outside the image sensor, and wherein the X-ray absorption layer is disposed proximate to the second side of the semiconductor layer; and
   forming one or more microlenses disposed proximate to the first side of the semiconductor layer, wherein the X-ray radiation and the image light propagate through the one or more microlenses, and wherein the microlenses focus the image light into the plurality of photodiodes.

16. The method of claim 15, wherein forming the X-ray absorption layer comprises depositing the X-ray absorption layer on the semiconductor layer.

17. The method of claim 15, wherein forming the X-ray absorption layer comprises bonding the X-ray absorption layer to the semiconductor layer.

* * * * *